United States Patent [19]

Christensen

[11] Patent Number: Plant 6,121

[45] Date of Patent: Mar. 8, 1988

[54] HYBRID TEA ROSE PLANT CV. AROMICLEA

[75] Inventor: Jack E. Christensen, Ontario, Calif.

[73] Assignee: Armstrong Nurseries, Inc., Somis, Calif.

[21] Appl. No.: 814,553

[22] Filed: Dec. 30, 1985

[51] Int. Cl.[4] ..... A01H 5/00

[52] U.S. Cl. ..... Plt./11

[58] Field of Search ..... Plt. 11

*Primary Examiner*—Robert E. Bagwill

*Attorney, Agent, or Firm*—William H. Elliott, Jr.; William T. King

[57] ABSTRACT

A new hybrid tea rose for garden decoration, having as its seed parent an undisseminated seedling of the cross [Camelot (U.S. Plant Pat. No. 2,371)×First Prize (U.S. Plant Pat. No. 2,774])×Typhoo Tea (U.S. Plant Pat. No. 3,845), and as its pollen parent, Lolita. The plant is a tall, very hardy outdoor seedling of the bush type, producing an abundance of large, sweetly scented blossoms that open yellow and peachy-orange, then develop a scarlet blush. The flowers' long, strong stems and urn-shaped buds make them very suitable for cutting. The plant's nearly continual bloom, unusually heavy, leathery and very glossy foliage, and well-branched habit make it an attractive garden plant, and its above-average vigor and superb disease resistance make it a low-maintenance plant, ideal for landscaping.

1 Drawing Sheet

This invention relates to a new variety of hybrid tea rose cv. Aromiclea. The plant is a tall, hardy outdoor seedling of the bush type, cultivated for garden decoration and very suitable for cut flower production. It was bred by Jack E. Christensen in Ontario, Calif., and has as its seed parent an undisseminated seedling of the cross [Camelot (U.S. Plant Pat. No. 2,371)×First Prize (U.S. Plant Pat. No. 2,774)]×Typhoo Tea (U.S. Plant Pat. No. 3,845), and as its pollen parent, Lolita.

The new variety cv. Aromiclea may be distinguished from other presently available commercial rose cultivars by the following combination of characteristics: its large blossoms of a unique chatoyant orange coloration, essentially as described and illustrated herein; its sweet flower scent, long, strong stems, and urn-shaped buds, which make the flowers very suitable for cutting; its unusually heavy, leathery and very glossy foliage; its nearly continual bloom and well-branched habit, which make it an attractive garden plant; and its vigor, above-average hardiness, well-above-average disease resistance, and attractive flower finish, which make it desirable as a low-maintenance plant for landscaping. Aromiclea holds these distinguishing characteristics through succeeding propagations by budding.

The new rose may be distinguished from its seed parent, an undisseminated seedling of the cross (Camelot×First Prize)×Typhoo Tea, by the following combination of characteristics: Whereas the seed parent bears flowers of a coral pink coloration with a distinct white underside, Aromiclea bears flowers of a chatoyant orange coloration, essentially as described and illustrated herein. The new variety bears flowers with 29 to 34 petals, whereas the parent seedling bears flowers of distinctly lighter petalage (20 to 25 petals). The parent plant produces a mature bush of medium height and upright-spreading habit, whereas the new cultivar produces a significantly taller bush of very upright habit.

The new variety may be distinguished from its pollen parent, Lolita, by the following combination of characteristics: Whereas Lolita produces flowers of a blended golden apricot coloration, Aromiclea produces flowers of a chatoyant orange coloration, essentially as described and illustrated herein. Lolita bears short flower buds that are ovoid in shape, whereas the new cultivar bears significantly longer flower buds with a more slender shape. Under the growing conditions of southern California, Lolita bears flowers of heavy petalage (40 to 45 petals), whereas Aromiclea bears flowers of significantly lighter petalage (29 to 34 petals).

The accompanying drawing illustrates the plant in color and shows the flowering thereof from bud to full bloom. Throughout this specification, color names beginning with a small letter signify that the name of that color as used in common speech is aptly descriptive. Color names beginning with a capital letter designate values based upon the R.H.S. Colour Chart of The Royal Horticultural Society of London, England.

The descriptive matter which follows pertains to roses of the new variety grown in southern California and is believed to apply to plants of the variety grown in similar conditions of soil and climate elsewhere.

FLOWER

The new variety usually bears its flowers singly, sometimes two to three flowers per stem, in irregular, rounded clusters. Flowers are borne on strong stems that are long for the class. Outdoors, the plant blooms very abundantly and nearly continuously during the growing season. It has a moderate, spicy to fruity fragrance.

BUD

The peduncle is of average length for the class, of average to heavy caliper, strong and erect. It is moderately smooth, with some stipitate glands, and between Yellow-Green 144B and Green 138A in color.

Before the calyx breaks, the bud is medium to large in size for the class, medium-length to long, and pointed in form. The surface of the bud bears a few foliaceous appendages and stipitate glands. Slender, shallowly serrate foliaceous parts are usually present, extending beyond the tip of the bud and equal to one half or more of its length.

As the calyx breaks, bud color is between Red 45C and Red 45B.

The inner surface of the sepals has a woolly tomentum; margins are lined with stipitate glands and hairs.

As the first petal opens, the bud is average to large in size for the class, long, and pointed to urn-shaped in form. The outside surface of the newly-opening petals displays a basal attachment zone near Yellow 12A that slowly suffuses to between Orange 24C and Greyed-Orange 170D and is often blushed with between Orange-Red 34C and Red 45B. The inside surface of the opening petals displays a smaller basal attachment zone near Yellow 12A, which quickly suffuses to between Orange-Red 30A and Greyed-Orange 170A. The bud opens up well and is not retarded or prevented from opening by cold, hot, wet, or dry weather.

BLOOM

When fully open, the bloom is large for the class, ranging from 4½ to 5½ inches in diameter. Petalage is double, with petals arranged regularly; there are from 29 to 34 petals present and from 1 to 6 petaloids. When half open, the bloom is very high-centered, and the petals are moderately cupped with petal edges moderately reflexed outward. When fully open, the bloom is somewhat cupped, with petals loosely cupped and petal edges undulated and reflexed outward.

The petals are of moderately heavy substance and thick, with insides slightly velvety and outsides slightly satiny. The outside petals are nearly round to broadly obovate in shape, sometimes scalloped, with rounded apices. The intermediate petals are broadly obovate and sometimes scalloped, with rounded apices. The inner petals are narrowly obovate, sometimes scalloped to irregular, with rounded apices. Petal colors may be modified by being bordered or blotched or shaded or washed or tinted with other colors.

The paragraphs immediately following describe the color values observed in a newly opened flower on a plant grown outdoors in Somis, Calif., in the month of September.

The outside surface of the outside petals displays a basal attachment zone near Yellow 9C that suffuses to between Orange 24C and Orange 29C and is often blushed with between Red 47B and Orange-Red 35A. The inside surface of the outside petals displays a basal attachment zone near Yellow 9C that slowly suffuses to between Orange-Red 35B and Yellow-Orange 20C, with petal edges blushed as deeply as between Orange-Red 34A and Red 45C.

The outside surfaces of the intermediate and inner petals have the same coloration as the outside surface of the outside petals, but without blushing.

The inside surface of the intermediate petals has the same coloration as the inside surface of the outside petals, but with less blushing. The inside surface of the inner petals has the same coloration as the inside surface of the outside petals, but with no blushing.

The paragraphs immediately following describe the color values observed in a bloom which had been open for three days on a plant grown outdoors in Somis, Calif., in the month of September.

The outside surfaces of the outside and inside petals display a basal attachment zone near Yellow 10A, which suffuses to between Yellow-Orange 23D and Orange-Red 33D with petal edges colored as deeply as near Red 47C. The inside surfaces of the outside and inside petals display a basal attachment zone near Yellow 10A which slowly suffuses to between Red 37C and Orange 29C and is predominantly blushed with between Red 40A and Red 45A.

In general, the blossoms exhibit a unique chatoyant orange coloration. The general color effect of the newly opened flower is between Orange-Red 35B and Yellow-Orange 20C, with outer petals blushed to between Orange-Red 34A and Red 45C. After three days, the general color effect of the flower is predominantly blushed to between Red 40A and Red 45A. The petals usually drop off cleanly and are not particularly affected by hot, wet, or dry weather.

In September, flowers on plants of the new variety grown in the garden last on the bush from 4 to 5 days. Flowers cut from plants grown outdoors in September last from 5 to 6 days at living-room temperatures.

REPRODUCTIVE ORGANS

Stamens are average in number and are arranged irregularly about the pistils; a few may be tucked in the calyx. The filaments are short to medium in length, and most have anthers. The anthers are of medium size, and all open at approximately the same time. Anther color is near Yellow-Orange 21A when immature and near Greyed-Orange 166A at maturity. Pollen is somewhat abundant.

Pistils are average in number (approximately 75). The styles are uneven, short to average in length, of average caliper, and somewhat bunched. The stigma is near Yellow-Orange 19A in color. Ovaries are usually all enclosed in the calyx.

Hips are of average length, ovoid to globular in form, and near Yellow 12B in color. They are very smooth and have thick, fleshy walls. The sepals fall soon. Seeds are medium to large in size and average in number (12 to 18).

FOLIAGE

The compound leaves are borne in very abundant quantities and usually comprise from three to five leaflets. The leaves are of small to medium size for the class, very heavy to somewhat leathery, and glossy. The leaflets are nearly oval in shape, with acute apices and round bases; their margins are simply serrate.

The upper surface of the mature foliage is between Yellow-Green 147A and Green 139A in color; its under surface is between Green 138A and Yellow-Green 146C. The upper surface of the young foliage is between Greyed-Purple 187A and Greyed-Purple 183A. The under surface of the young foliage is near Greyed-Purple 183C.

The rachis is average in size to heavy, grooved on its upper side, with some stipitate glands on its edges. The under side of the rachis is moderately prickly and bears stipitate glands.

Stipules are medium to long in length, of medium width, and have medium-length to long points turning out at an angle of usually less than 45°. The undersides of the stipules bear many stipitate glands.

The plant displays a more-than-average resistance to mildew, rust and blackspot as compared to other commercial varieties grown under comparable conditions in Somis, Calif.

GROWTH

The plant is of tall, bushy, upright, and much-branched habit. It displays very vigorous growth. The canes are of heavy caliper for the class.

The main stems are between Yellow-Green 146D and Green 138B in color. They bear many large prickles which are moderately short for the class. The large prickles are almost straight to hooked slightly downward and have moderately long, broad bases; prickle color is near Greyed-Orange 165B. The main stems bear many small prickles, also near Greyed-Orange 165B in color, and have no hairs.

The branches are of a color between Yellow-Green 146B and Green 138A. They bear many moderately short large prickles, which are almost straight to hooked slightly downward, with moderately long, broad bases. The large prickles are near Greyed-Yellow 162A in color. The branches have many small prickles near Greyed-Yellow 167A in color and no hairs.

New shoots are between Greyed-Purple 187A and Greyed-Purple 183A in color. They bear many moderately short large prickles which are almost straight to hooked slightly downward, with moderately long, broad bases. Prickle color is near Greyed-Red 178B. There are many small prickles near Greyed-Red 178B in color; there are no hairs.

I claim:

1. The new and distinct variety of hybrid tea rose plant cv. Aromiclea and the parts thereof, substantially as shown and described herein, the plant being particularly characterized by its large blossoms of a unique chatoyant orange coloration, essentially as described and illustrated herein; its sweet, moderately spicy to fruity fragrance, long, strong stems, urn-shaped buds, and attractive flower finish; its unusually heavy, leathery and very glossy foliage; its nearly continual bloom and well-branched habit; and its vigor, above-average hardiness, and well-above-average disease resistance.

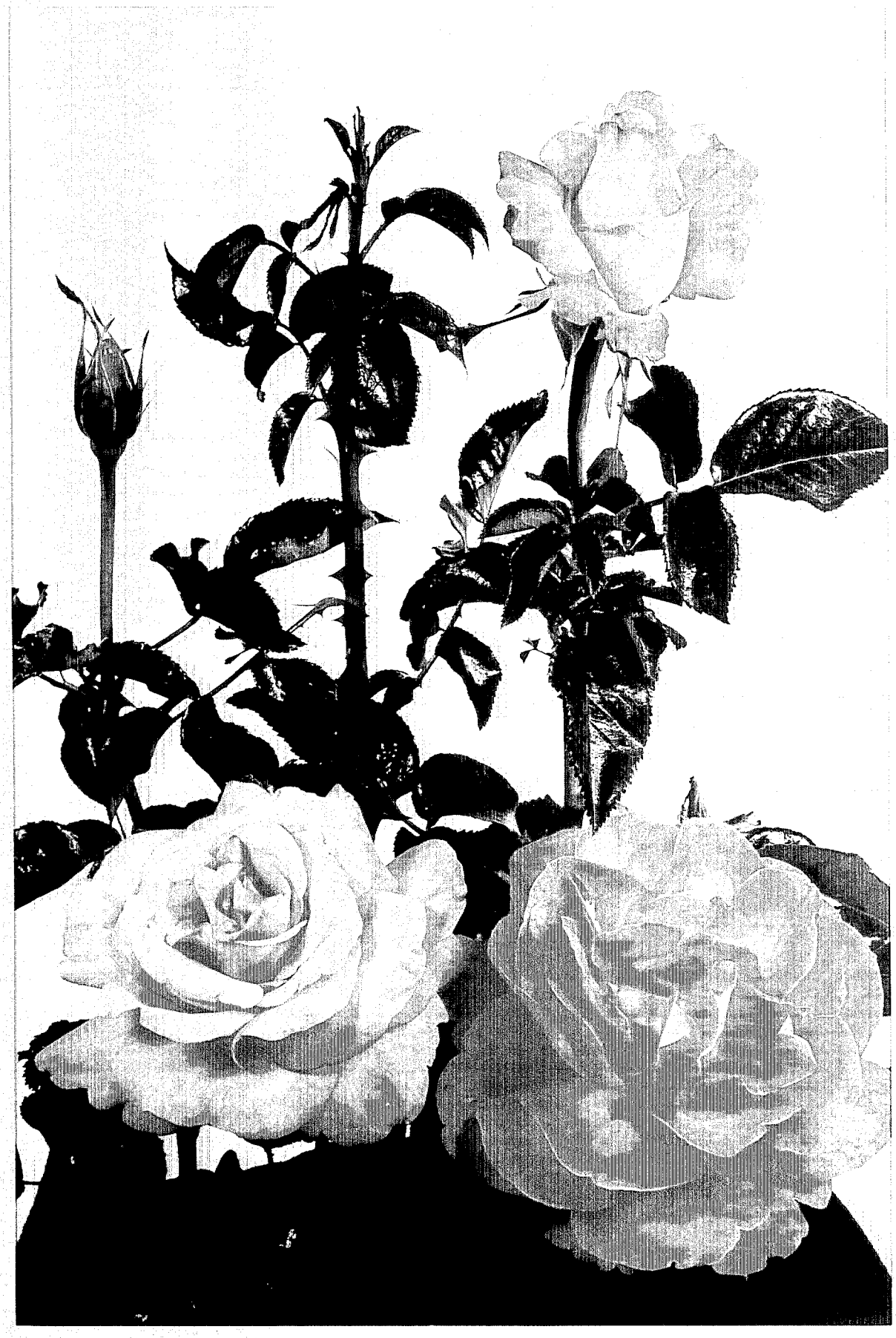

* * * * *